United States Patent
Palti et al.

(10) Patent No.: US 11,771,505 B2
(45) Date of Patent: *Oct. 3, 2023

(54) THREE DIMENSIONAL MAPPING SYSTEM FOR CRANIAL SURGICAL PATHWAYS AND METHOD

(71) Applicant: Biosense Webster (Israel) Ltd., Yokneam (IL)

(72) Inventors: Yair Palti, Herzelia (IL); Remi Bettan, Haifa (IL); Vadim Gliner, Haifa (IL); Uri Avni, Ram-on (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 857 days.

This patent is subject to a terminal disclaimer.

(21) Appl. No.: 16/731,524

(22) Filed: Dec. 31, 2019

(65) Prior Publication Data

US 2021/0196405 A1 Jul. 1, 2021

(51) Int. Cl.
*A61B 5/00* (2006.01)
*A61B 34/00* (2016.01)
(Continued)

(52) U.S. Cl.
CPC .............. *A61B 34/25* (2016.02); *A61B 17/24* (2013.01); *A61B 34/20* (2016.02); *G06T 15/08* (2013.01);
(Continued)

(58) Field of Classification Search
CPC ........... G06T 7/187; G06T 7/181; G06T 7/10; G06T 7/12; G06T 2207/301
See application file for complete search history.

(56) References Cited

U.S. PATENT DOCUMENTS 5,611,025 A 3/1997 Lorensen
7,167,180 B1 * 1/2007 Shibolet ................... G06T 7/13
345/474
(Continued)

FOREIGN PATENT DOCUMENTS

EP 1057161 A1 12/2000
EP 2707851 A2 3/2014
(Continued)

OTHER PUBLICATIONS

International Search Report and Written Opinion of the International Searching Authority dated Mar. 31, 2021 for PCT International Application No. PCT/IB2020/061939.

*Primary Examiner* — Rajeev P Siripurapu
(74) *Attorney, Agent, or Firm* — Volpe Koenig

(57) ABSTRACT

Apparatus and methods are provided for mapping and displaying three dimensional surgical pathways within imaging of cranial structures derived from voxels of a cranial scan. Entry voxel and target voxel are selected as pathway endpoints. A series of respective neighbor voxels are mapped between the entry voxel and the target voxel to define a pathway. For each voxel $Vx_i,y_i,z_i$ in the series, an immediately succeeding voxel of voxel $Vx_i,y_i,z_i$ is selected from among the group of neighbor voxel of voxel $Vx_i,y_i,z_i$ which excludes neighbor voxels of the immediately preceding voxel of voxel $Vx_i,y_i,z_i$. The selection is made by comparing selection weights determined based on relative distances with respect to the endpoint voxels and relative distance from voxels within a predetermined distance that represent at least a threshold density. The voxels of the pathway are then selectively highlighted in a displayed view to provide a visualization of the 3D surgical pathway.

20 Claims, 8 Drawing Sheets

(51) Int. Cl.
 *A61B 34/20* (2016.01)
 *A61B 17/24* (2006.01)
 *G06T 15/08* (2011.01)
(52) U.S. Cl.
 CPC ............ *A61B 2034/2055* (2016.02); *A61B 2034/2072* (2016.02); *A61B 2034/254* (2016.02); *G06T 2210/41* (2013.01)

(56) References Cited

U.S. PATENT DOCUMENTS

| | | | |
|---|---|---|---|
| 2004/0109603 A1* | 6/2004 | Bitter | G06T 15/10 382/154 |
| 2004/0209234 A1 | 10/2004 | Geiger | |
| 2007/0024617 A1* | 2/2007 | Poole | G06T 7/181 345/424 |
| 2008/0123922 A1 | 5/2008 | Gielen | |
| 2015/0257847 A1 | 9/2015 | Higgins | |
| 2017/0148213 A1 | 5/2017 | Thomas | |
| 2018/0055582 A1 | 3/2018 | Krimsky | |

FOREIGN PATENT DOCUMENTS

| | | |
|---|---|---|
| WO | 99/42977 A1 | 8/1999 |
| WO | 2012/153249 A2 | 11/2012 |

* cited by examiner

THREE DIMENSIONAL MAPPING SYSTEM FOR CRANIAL SURGICAL PATHWAYS AND METHOD

FIELD OF INVENTION

The present application provides systems, apparatuses, and methods for improving medical procedures.

BACKGROUND

Visualization of internal body structures can be performed by mapping propagation of activation waves. Fluoroscopies, computerized tomography (CT), ultrasound and magnetic resonance imaging (MRI), as well as other techniques may be utilized to provide the visualization and graphical renderings of intra-body structures.

Typically, visualization and graphical renderings of intra-body structures are comprised of voxels of a 3D scan image; a voxel being imaging data of a selected coordinate of a particular slice of a scan. For, example, a cranial CT scan can produce a series of image "slices" of a subject's head comprised of voxels of imaging data which each represent a type of material such as bone, tissue, air etc. The scan slices are combined in sequence produce to a 3D scan image of the subject's head and its internal and external structures from the cranial scan.

The type of material represented by a voxel is conventionally determined by applying selected analytical criteria to the scan data, such as applying the well know Hounsfield scale. A color or grey scale weight can then be selected to correspond to the determined represented material to present a realistic image of the scanned skull on a display device.

With the use of modern computer processors, which may include both computer processing units (CPUs) and graphic processing units (GPUs), a user can operate a display device to view virtually any cross-section or perspective view of the 3D scan image of the skull derived from the scan data. Such views can also be printed as may be desired including with 3D printing technology to produce and actual 3D rendering.

A variety of medical conditions can require surgery within the cranium of a subject. For example, an ENT (ear, nose, throat) physician may diagnose an ailment requiring surgery at a relatively remote site in a patients sinuses.

To prepare for such a surgery, it is desirable to provide a visualization and three dimensional (3D) map of a pathway to the surgical site. The pathway being one through which surgical tools can be inserted for non-invasive surgery at the remote surgical site within the cranium where the pathway does not pass through bone, tissue or other such barrier. While multiple such pathways may exist, it is preferred that a pathway be selected that is relatively short while maintaining as much distance from bone as may be possible.

SUMMARY

A system, apparatus and methods are provided for mapping and displaying a three dimensional (3D) surgical pathway within displayed imaging of cranial structures derived from voxels of a cranial scan of a subject.

In an example method, an initial entry voxel $Vx_e,y_e,z_e$ and a surgical site target voxel $Vx_t,y_t,z_t$ are selected as endpoints of the 3D surgical pathway. A series of voxels are mapped such that each voxel between the entry voxel $Vx_e,y_e,z_e$ and the target voxel $Vx_t,y_t,z_t$ is a neighbor voxel of both an immediately preceding voxel and an immediately succeeding voxel of the series to define the 3D surgical pathway. For each voxel $Vx_i,y_i,z_i$ in the series having an immediately preceding voxel, the immediately succeeding voxel of voxel $Vx_i,y_i,z_i$ is selected from among the group of neighbor voxel of voxel $Vx_i,y_i,z_i$ which excludes neighbor voxels of the immediately preceding voxel of voxel $Vx_i,y_i,z_i$.

The selection includes determining selection weights of each voxel of the group of neighbor voxel on a selected basis. The basis of voxel selection includes relative distances with respect to the endpoint voxels $Vx_e,y_e,z_e$ and $Vx_t,y_t,z_t$ and relative distance d from voxels within a predetermined distance p that represent at least a threshold density. The immediately succeeding voxel of voxel $Vx_i,y_i,z_i$ is then selected based on a comparison of the determined selection weights. The voxels of the determined 3D surgical pathway are then selectively highlighted in a displayed view of the cranial structure to provide a visualization of the 3D surgical pathway.

The selection basis for determining selection weights for a voxel can include a penalty where a voxel that represents at least the threshold density is within the predetermined distance. The penalty can be based on the difference between the predetermined distance p and the distance d of the voxel from the closest voxel that represents at least the threshold density. In one example, the threshold density is set as minus five hundred (−500) Hu and the predetermined distance p is 0.8 mm. In another example, the threshold density is set to be the density of bone.

The 3D surgical pathway may be determined starting at the entry voxel $Vx_e,y_e,z_e$. In such case, selection weights of each voxel of the group of neighbor voxels of each voxel $Vx_i,y_i,z_i$ can be determined on a selected basis that includes relative closeness to the entry voxel $Vx_e,y_e,z_e$ and relative distance from the target voxel $Vx_t,y_t,z_t$.

Alternatively, the 3D surgical pathway may be determined starting at the target voxel $Vx_t,y_t,z_t$. In such case, selection weights of each voxel of the group of neighbor voxels of each voxel $Vx_i,y_i,z_i$ can be determined on a selected basis includes relative distance from the entry voxel $Vx_e,y_e,z_e$ and relative closeness to the target voxel $Vx_t,y_t,z_t$.

The selective highlighting of the voxels of the 3D surgical pathway in a displayed view of the cranial structure can include applying different highlighting of voxels of portions of the 3D surgical pathway that are hidden in the displayed view.

The method of claim 1 can further include using the displayed view of the 3D surgical pathway to insert a distal end of a catheter into the cranium of the subject along the 3D surgical pathway, starting at a physical location in the subject's cranium corresponding to the initial entry voxel $Vx_e,y_e,z_e$, to deploy the distal end of the catheter to a physical location corresponding to the surgical site target voxel $Vx_t,y_t,z_t$.

An example apparatus for mapping and displaying a three dimensional (3D) surgical pathway within a graphic display of a cranial structure derived from voxels of a cranial scan of a subject includes a processor and associated data storage, display, and voxel selection devices. The data storage is configured to store voxels of the cranial scan of the subject. The processor and the associated display device are configured to provide sectional and perspective views of cranial structures of the subject based on the cranial scan. The voxel selection device is configured for a user to select an initial entry voxel $Vx_e,y_e,z_e$ and a surgical site target voxel $Vx_t,y_t,z_t$ as endpoints of the 3D surgical pathway.

The processor is further configured to map a series of voxels such that each voxel between the entry voxel $Vx_e,y_e,z_e$ and the target voxel $Vx_t,y_t,z_t$ is a neighbor voxel of both an immediately preceding voxel and an immediately succeeding voxel of the series to define the 3D surgical pathway. For each voxel $Vx_i,y_i,z_i$ in the series having an immediately preceding voxel, the processor is configured to select the immediately succeeding voxel of voxel $Vx_i,y_i,z_i$ from among the group of neighbor voxel of voxel $Vx_i,y_i,z_i$ which excludes neighbor voxels of the immediately preceding voxel of voxel $Vx_i,y_i,z_i$.

The selection is performed by determining selection weights of each voxel of the group of neighbor voxel on a selected basis including relative distances with respect to the endpoint voxels $Vx_e,y_e,z_e$ and $Vx_t,y_t,z_t$ and relative distance from voxels within a predetermined distance that represent at least a threshold density and then selecting the immediately succeeding voxel of voxel $Vx_i,y_i,z_i$ based on a comparison of the determined selection weights.

The processor is further configured to selectively highlight the voxels of the determined 3D surgical pathway in imaging of cranial structures on the display device to provide a visualization of the 3D surgical pathway.

The processor can be configured such that the selected basis used by the processor for the determining selection weights for a voxel includes a penalty where a voxel that represents at least the threshold density is within the predetermined distance. The processor can be configured to determine the penalty based on the difference between the predetermined distance and the distance of the voxel from the closest voxel that represents at least the threshold density. In one example, the threshold density is set as minus five hundred (−500) Hu and the predetermined distance is 0.8 mm.14. In another example, the threshold density is set to be the density of bone.

The processor can be configured such that the 3D surgical pathway is determined starting at the entry voxel $Vx_e,y_e,z_e$. In such case, selection weights of each voxel of the group of neighbor voxels of each voxel $Vx_i,y_i,z_i$ are determined on a selected basis that includes relative closeness to the entry voxel $Vx_e,y_e,z_e$ and relative distance from the target voxel $Vx_t,y_t,z_t$.

The processor can alternatively be configured such that the 3D surgical pathway is determined starting at the target voxel $Vx_t,y_t,z_t$. In such case, selection weights of each voxel of the group of neighbor voxels of each voxel $Vx_i,y_i,z_i$ are determined on a selected basis that includes relative distance from the entry voxel $Vx_e,y_e,z_e$ and relative closeness to the target voxel $Vx_t,y_t,z_t$.

The processor can also be configured such that the selective highlighting of the voxels of the 3D surgical pathway in a displayed view of the cranial structure includes applying different highlighting of voxels of portions of the 3D surgical pathway that are hidden in the displayed view.

The example apparatus can further include a catheter having a distal end from which a surgical tool can be operated and associated catheter location sensing equipment coupled to the processor. The location sensing equipment is configured to provide signals that enable the processor to track the location of the distal end of the catheter as it is inserted into the subject's cranium. In this case, the processor is configured to control the display device to display a corresponding visualization of catheter travel such that a user is enabled to use a displayed view of the 3D surgical pathway to insert the distal end of the catheter into the cranium of the subject along the 3D surgical pathway, starting at a physical location in the subject's cranium corresponding to the initial entry voxel $Vx_e,y_e,z_e$, to deploy the distal end of the catheter to a physical location corresponding to the surgical site target voxel $Vx_t,y_t,z_t$.

BRIEF DESCRIPTION OF THE DRAWINGS

A more detailed understanding can be had from the following description, given by way of example in conjunction with the accompanying drawings.

DETAILED DESCRIPTION

According to implementations of the disclosed subject matter, imaging data in the form of voxels of a scan of a subject's head is used to derive a visualization and three dimensional (3D) map of a pathway to a desired site, such as an internal cranial site where a surgical procedure is to be performed.

For reference herein, voxels can be represented by the notation Vx,y,z where z indicates a particular slice in the series of imaging slices derived from the scan, and x and y are coordinates with in the z slice. The order of the subscripts x, y, and z in the Vx,y,z notation is used by way of example and is not intended to be limiting. For example, Vz,y,x could be as the form of notation.

Figure 1A:
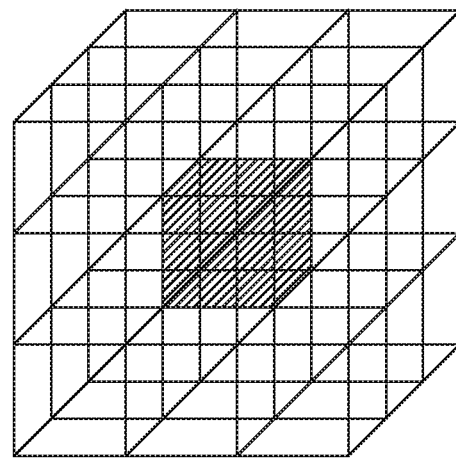
FIG. 1A is an illustration of a voxel and its neighbor voxels of a 3D image derived from a scan.

A voxel Vx,y,z may be viewed as a cube that generally is surrounded by twenty-six other voxels where the voxel Vx,y,z is in the center of a 3×3 cubic array of voxels, as illustrated in FIG. 1A. The exceptions being where x or y represent a coordinate at an edge of the slice z or where z is the first or last slice of the series of imaging slices.

Figure 1B:
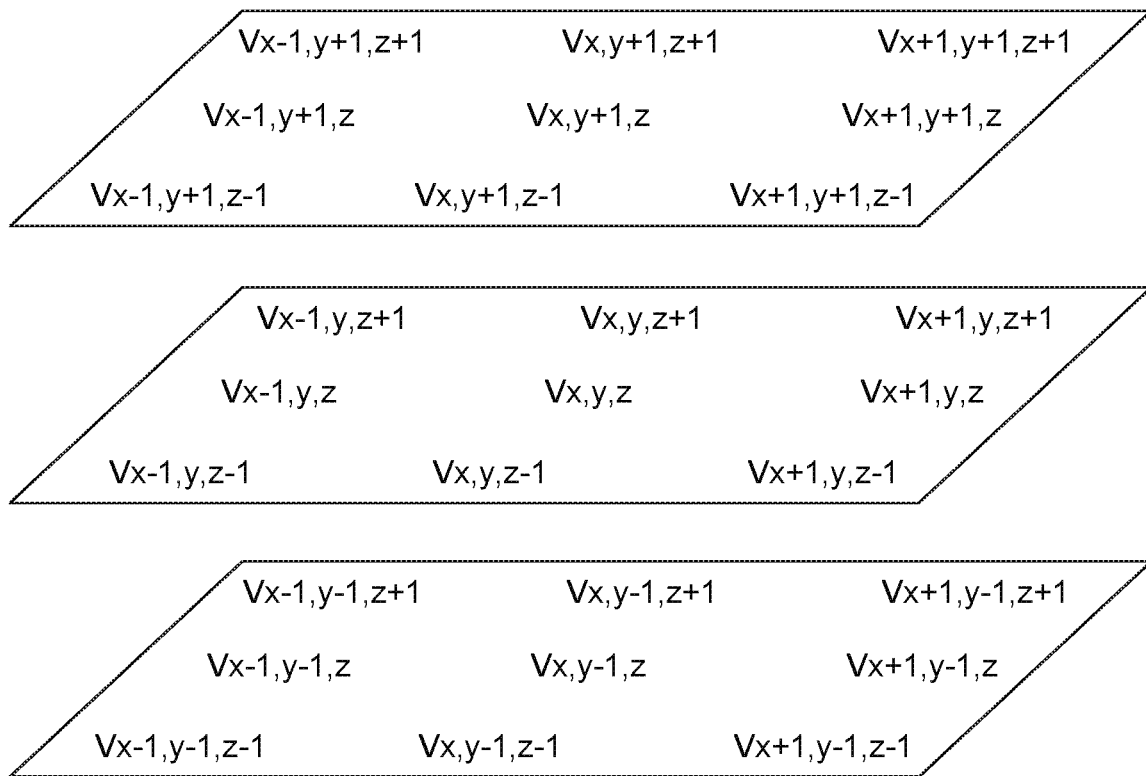
FIG. 1B is a graphic representation for an example notations representing corresponding voxels of FIG. 1A.

The twenty-six surrounding voxels of voxel Vx,y,z are herein referred to as "neighbor voxels." It will be recognized that the twenty-six neighbor voxels of voxel Vx,y,z consist of:

six "adjacent neighbor" voxels, namely voxels Vx+1,y,z, Vx−1,y,z, Vx,y+1,z, Vx,y−1,z, Vx,y,z−1, and Vx,y,z+1;

twelve "2D diagonal neighbor" voxels, namely voxels Vx+1,y+1,z, Vx+1,y−1,z, Vx−1,y+1,z, Vx−1,y−1,z, Vx,y+1,z+1, Vx,y−1,z+1, Vx+1,y,z+1, Vx−1,y,z+1, Vx,y+1,z−1, Vx,y−1,z−1, Vx+1,y,z−1, and Vx−1,y,z−1; and eight "3D diagonal neighbor" voxels, namely voxels Vx+1,y+1,z+1, Vx−1,y+1,z+1, Vx+1,y−1,z+1, Vx−1,y−1,z+1, Vx+1,y+1,z−1, Vx−1,y+1,z−1, Vx+1,y−1,z−1, and Vx−1,y−1,z−1;

as illustrated in FIG. 1B.

A surgical pathway from an initial entry site starting at a voxel $Vx_e,y_e,z_e$ to a surgical target site at voxel $Vx_t,y_t,z_t$ is defined by a series of voxels where each voxel between voxels $Vx_e,y_e,z_e$ and voxel $Vx_t,y_t,z_t$ is a neighbor voxel of both its immediately preceding voxel and its immediately succeeding voxel of the series defining the pathway.

Figure 2:
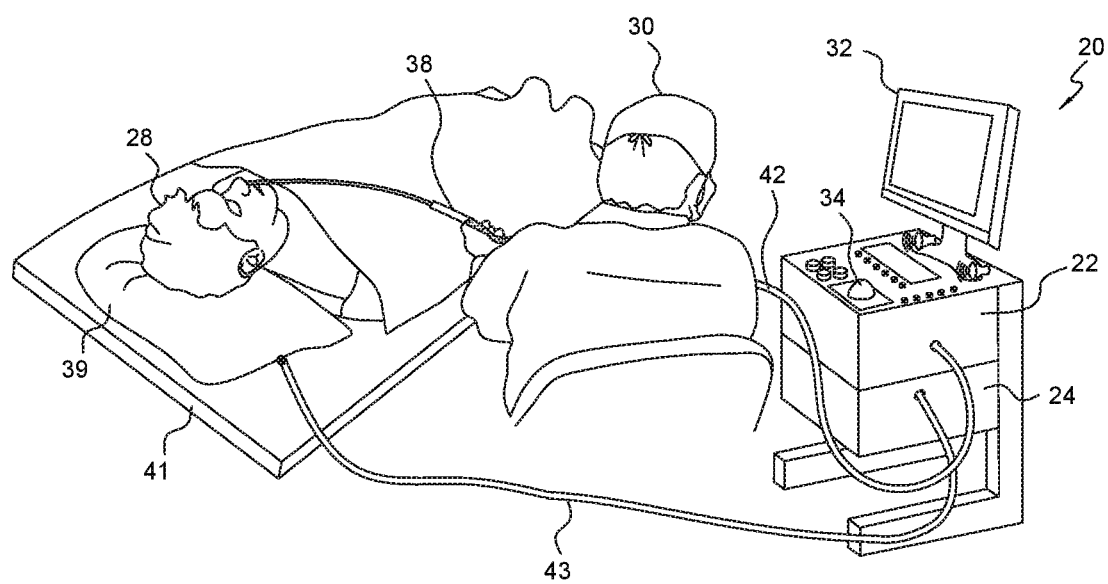
FIG. 2 is a diagram of an exemplary system in which one or more features of the disclosure subject matter can be implemented.

FIG. 2 is a diagram of an exemplary mapping system 20 in which one or more features of the disclosure subject matter can be implemented. The mapping system 20 includes a data processing component 22 and a data storage component 24 configured to process and store 3D scan images. For example, a 3D scan image derived from imaging data of a scan of a head 26 of a patient 28 for whom an ENT (ear/nose/throat) physician 30 is to perform a non-invasive surgical operation at a selected site within the patient's head 26.

The mapping system 20 includes a monitor or other display device 32 for selectively displaying, for example, selected cross-section or perspective views from the 3D scan image of the patient's head 26. The data processing component 22 can include one or more CPUs, GPUs and/or other processors that are coupled to the data storage component 24 and display device 32 to produce desired cross-section or perspective views on the display device 32 from a 3D scan image, such as derived from scan data of the patient's head 26.

For 3D-like perspective views displayed the display device 32, where the display device employs a Cartesian pixel display, the voxels are appropriately mapped to the pixels to provide perspective views which appear to have three dimensions using conventional GPU technology. However, where a holographic or other true 3D display device is used, the voxels can be directly mapped to 3D coordinate display elements.

The data processing component 22 is further configured to control the display device to display 3D surgical pathways between selected voxels in a displayed view through applying a predetermined attribute, for example a solid color, to the displayed voxels defining the particular 3D surgical pathway, which is referred to herein as highlighting the voxels of the 3D surgical pathway.

If in a particular view a portion of the pathway lies beneath barrier voxels such as bone or tissue, that portion of the pathway may be differently highlighted, such as with a different color, to indicate that the pathway portion is actually hidden behind barrier material such as bone or tissue. In such case, the ENT physician may wish to select a different view of the 3D scan image where the previously hidden portion of the pathway is not behind barrier material.

Figure 9:
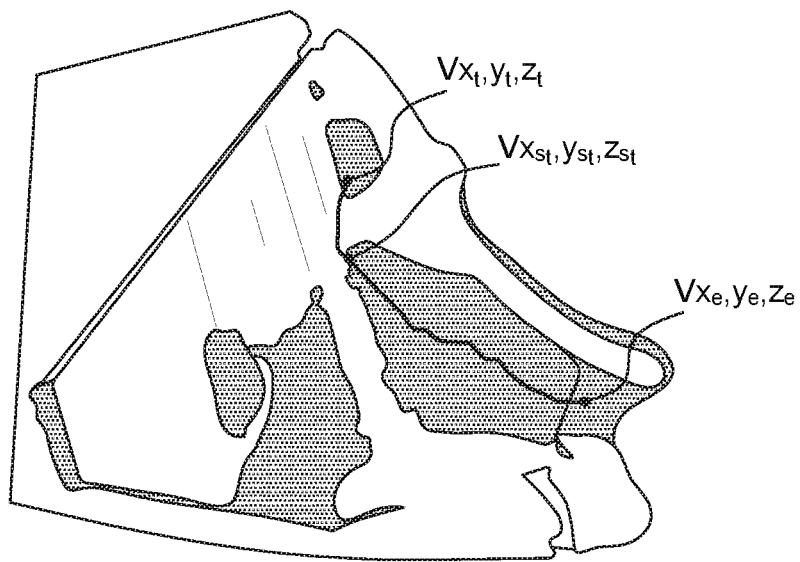
FIG. 9 is a graphic depiction of a displayed view corresponding to the displayed view of FIG. 3 illustrating a surgical path between endpoints derived in accordance with another example of the teachings of the present invention.

For example, with respect to view illustrated in FIG. 9, a portion of a determined pathway illustrated between the voxel $Vx_{st},y_{st},z_{st}$ and the voxel $Vx_t,y_t,z_t$ appears to be passing over bone material. If the pathway portion that appears to be passing over bone material was actually determined to be in a passage lying beneath the bone material, different highlighting is preferably applied by the processing component 22 such that the displayed view reflects the actual relative position that the portion of the pathway beneath the displayed bone material.

The mapping system 20 includes one or more peripheral devices, such as a track ball and/or touch pad 34, to permit a user to select a particular view of, for example, the 3D imaging data of the scan of head 26 to display on the display device 32. On or more of the peripheral devices, such as device 34, is also configured to permit a user to select specific voxels which serve as end points of a pathway therebetween. Such peripheral devices can include, but are not limited to, computer mouse devices, video gaming controller devices, joystick devices, laser pointing devices, voice command devices and touch screen display controls. Preferably, one or more peripheral devices are employed to permit the user, such as the ENT physician 30 or a surgical assistant, to pan through consecutive views of the 3D scan image as may be desired an to select a target voxel at which to deploy a surgical tool to perform a surgical procedure.

The mapping system 20 may also include devices, such as a catheter 38 which includes a surgical tool or through which a surgical tool can be inserted for operation thereof at a distal end of the catheter 38. The catheter 38 can include ultrasound transducer configured to obtain biometric data or ultrasound slices or the like. The distal end of the catheter 38 can include a probe that operates in connection with a location pad 39 the disposed on a gurney 41 which the patient 28 is placed for the surgical procedure.

In the illustrated example of FIG. 2, the distal end probe of the catheter 38 and the location pad 39 comprise location sensing equipment and are coupled to the processing component 22 by respective cables 42, 43. In this example, the processing component 22 is configured to use signals from the catheter probe and location pad 29 to track the location of the distal end of the catheter 38 as it is inserted by the ENT physician 30 into the subject's cranium and to display a visualization of the catheter travel on the display device 32 in connection with the view of the 3D scan image being displayed.

In this manner, the ENT physician 30 can use the displayed view to follow a determined 3D surgical pathway from an initial entry site starting at a voxel $Vx_e,y_e,z_e$ to a surgical target site at voxel $Vx_t,y_t,z_t$ in the positioning of a surgical tool for the surgical procedure. Accordingly, with reference to the displayed view, the ENT physician 30, starting at a physical location in the subject's cranium corresponding to the initial entry site, inserts the distal end of the catheter 38 along the pathway to deploy the distal end of the catheter at a physical location corresponding to the target site by following the displayed pathway. At that point, the surgical tool is properly located for the surgical procedure if it is already disposed at the distal end of the catheter or the surgical tool can be inserted through the catheter for operation at the target site.

As indicated above, a pathway for non-invasive cranial surgery is determined by selecting an initial entry site, a voxel $Vx_e,y_e,z_e$, and a surgical target site, voxel $Vx_t,y_t,z_t$, as endpoints. The path is then defined by a series of voxels where each voxel between voxels $Vx_e,y_e,z_e$ and voxel $Vx_t,y_t,z_t$ is a neighbor voxel of both its immediately preceding voxel and its immediately succeeding voxel of the series defining the pathway.

Conventionally, starting with one of the endpoint voxels, and finishing when the other endpoint is reached, a next voxel in the pathway series is determined by selecting a "best" successor voxel from among the twenty-six neighbor voxels using what is known as the A-Star algorithm.

The A-star algorithm is a well-known algorithm for search of path in the mapping of the CT scans. The main parameters set in A-Star algorithm are in the equation: F=G+H. The F, G, and H variables are attributed to each voxel and are calculated for each neighbor voxel in connection with selecting a successor voxel of the pathway series of voxels. Where a neighbor voxel is a barrier voxel such a representing bone or tissue, that voxel is automatically excluded from consideration as the next voxel in the series.

F is the weight of the voxel. G is the distance between the voxel the start endpoint voxel. H is a heuristic—estimated distance from the voxel to the finish endpoint voxel.

In addition to the F, G and H parameters, two lists of voxels are maintained in implementing in the algorithm: an open list and a closed list. The open list is a list that contains selectable voxels that have been evaluated, but have not had all possible successor voxels evaluated. This is a list of pending tasks.

The closed list is a list which contains voxels that have been evaluated and all possible successor voxels have been evaluated and added to the the open list where applicable.

The A-Star Algorithm is started by first adding the starting endpoint voxel $Vx_e,y_e,z_e$ to the open list.

The following steps are repeated:
a. Select the voxel with the lowest cost (F) in the open list. This is called the current voxel.
b. Switch the current voxel to the closed list.
c. For each of the twenty six neighbor voxels of the current voxel:
   i. if the neighbor voxel is not selectable (tissue, bone, or other barrier voxel type) or if the neighbor voxel is in the closed list, ignore it.
   ii. if the neighbor voxel isn't in the open list, add the neighbor voxel to the open list. Make the current voxel the predecessor voxel of the neighbor voxel and determine and record the F, G, and H costs of the neighbor voxel.
   iii. if the neighbor voxel is in the open list already, check to see if the path to the neighbor voxel is better, using G cost as the measure. A lower G cost means that this is a better path. If so, change the predecessor voxel of the neighbor voxel to the current voxel, and recalculate the G and F costs of the node. If the open list is kept sorted according to the cost F, it may need resort to account for the change.

The process stops when the target voxel $Vx_t,y_t,z_t$ is added to the closed list, in which case the path has been found. Alternatively, the process stops when the open list is empty in which case the algorithm has failed to find the target voxel $Vx_t,y_t,z_t$ because there is no acceptable path.

Where the target voxel $Vx_t,y_t,z_t$ is found, working backwards from the target voxel $Vx_t,y_t,z_t$, the series of voxels from each closed list voxel to its predecessor voxel until the starting voxel $Vx_e,y_e,z_e$ is reached is saved as the path.

Since all twenty six neighbor voxels are considered to select the next voxel in the series, the process is computationally complex and relatively time and resource consuming.

Figure 3:
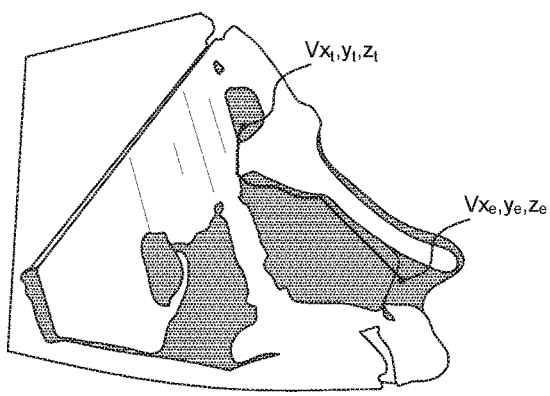
FIG. 3 is a graphic depiction of a selected displayed view illustrating a surgical path between endpoints derived in a conventional manner.

FIG. 3 illustrates a displayed view of a voxel path determined using the conventional A-Star Algorithm starting from entry site voxel $Vx_e,y_e,z_e$ to the surgical site target voxel $Vx_t,y_t,z_t$. The voxels in the conventionally determined path have been highlighted by processing unit 22 so that a continuous line representing the determined path between the entry site voxel $Vx_e,y_e,z_e$ and the target voxel $Vx_t,y_t,z_t$ is displayed.

As shown in FIG. 3, the conventionally determined path travels closely along nasal bone. As such, inserting the catheter 38 along the conventionally determined path increases the difficulty of operation of surgical tools at the target site.

In accordance with embodiments of the present invention, the processing component 22 is configured to perform cranial path mapping for defining a desired surgical pathway in a faster, less computationally complex manner which also provide better spacing from bone and/or other barrier voxels.

Figure 4:
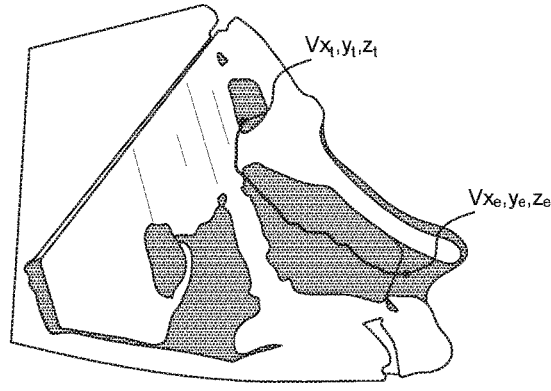
FIG. 4 is a graphic depiction of a displayed view corresponding to the displayed view of FIG. 3 illustrating a surgical path between endpoints derived in accordance with an example of the teachings of the present invention.

For example, FIG. 4 illustrates a displayed view of a voxel path determined using a modified A-Star Algorithm starting from the same entry site voxel $Vx_e,y_e,z_e$ to the same surgical site target voxel $Vx_t,y_t,z_t$, of FIG. 3. The voxels in the determined path of FIG. 4 have been highlighted by processing unit 22 so that a continuous line representing the determined path between the entry site voxel $Vx_e,y_e,z_e$ and the target voxel $Vx_t,y_t,z_t$ is displayed.

In the example implementation of the invention that produced the path illustrated in FIG. 4, the equation F=G+H was still employed with the F value remaining as F=G+H. However, the G value was the sum of the distance from the starting endpoint voxel to the current voxel plus a penalty that is a function to the voxel's proximity to voxels of at least a threshold density such as voxels representing tissue or bone. The H value was the Euclidean distance from the current voxel to the finishing endpoint voxel.

As shown in FIG. 4, the example determined path traverses nasal cavities a substantial distance from the illustrated bones where possible. As such, inserting the catheter 38 along the determined path decreases the difficulty of operation of surgical tools at the target site.

Although it is preferred to start with the entry site voxel $Vx_e,y_e,z_e$, as the starting endpoint voxel and the target site voxel $Vx_t,y_t,z_t$, as the finishing endpoint voxel, the process can be implemented with the entry site voxel $Vx_e,y_e,z_e$, as the finishing endpoint voxel and the target site voxel $Vx_t,y_t,z_t$, as the starting endpoint voxel.

One example of a penalty P which added in determining the G value is given by P equals the maximum of the values 0.0 mm or (p–d), where p is a predetermined distance for a desired minimum spacing from relatively dense material and d is the distance between the current voxel and a closest voxel representing a density of at least a threshold density.

For example, the threshold density can be set to measure distance to voxels having at least a Hounsfield value of minus five hundred (−500 HU) or greater, which includes voxels representing bone, tissue and other barrier substances. If desired, the threshold can be set as the density of a specific substance, such as the density of bone, tissue or another type of barrier substance.

The predetermined distance p, for example, can be set as 0.8 mm. In such case, if the current voxel is further than 0.8 mm distant from the closest voxel relatively dense voxel (i.e. one of at least the threshold density), no penalty is added to the usual G value. Accordingly, the penalty is computed in the 3D space, finding the distance d from the current voxel to any relatively dense voxel in all directions within sphere of radius p, which in this example is an 0.8 mm radius sphere.

Figure 6A:
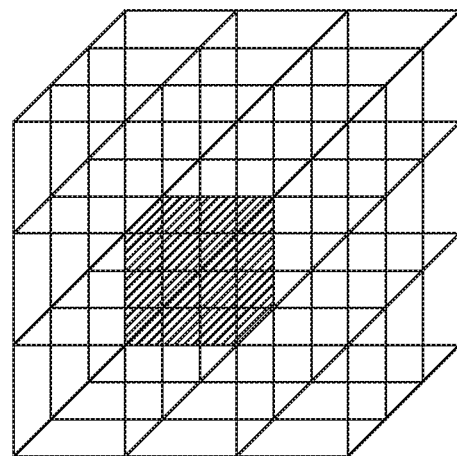
FIGS. 6A and 6B are graphic depiction of a first case of relative locations of an immediately preceding voxel FIG. 6A relative to a voxel FIG. 6B for which a successor voxel is to be determined.
Figure 6B:
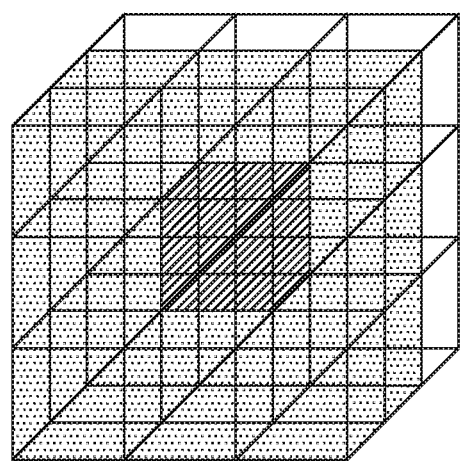
Figure 7A:
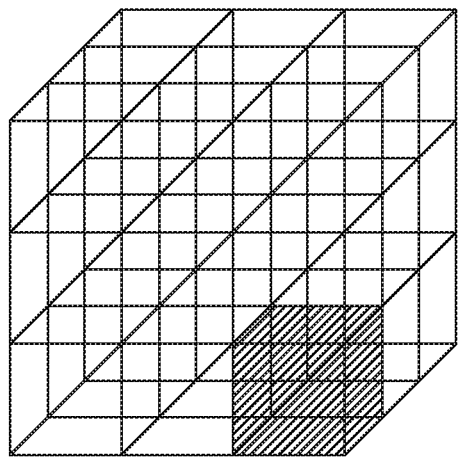
FIGS. 7A and 7B are graphic depiction of a second case of relative locations of an immediately preceding voxel FIG. 7A relative to a voxel FIG. 7B for which a successor voxel is to be determined.
Figure 7B:
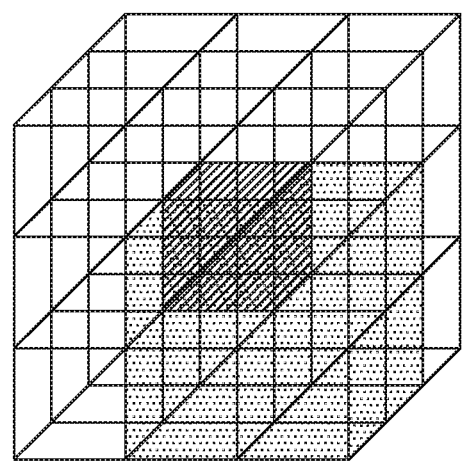
Figure 8A:
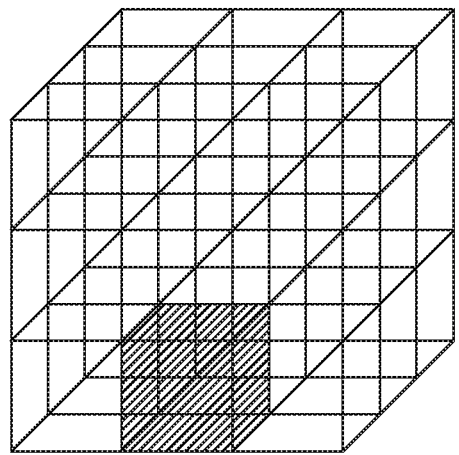
FIGS. 8A and 8B are graphic depiction of a third case of relative locations of an immediately preceding voxel FIG. 8A relative to a voxel FIG. 8B for which a successor voxel is to be determined.
Figure 8B:
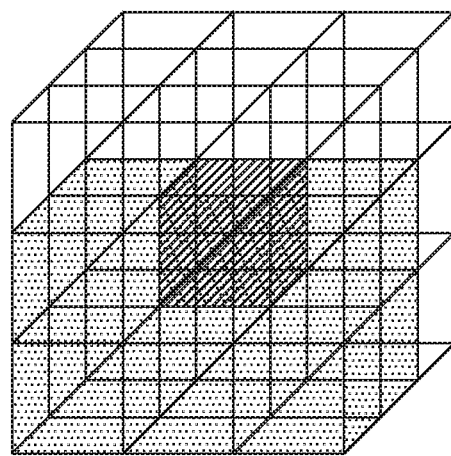

To reduce the computational complexity of the manner of mapping, in implementing a modified A-Star algorithm, the number of neighbor voxels evaluated with respect to the current voxel automatically eliminates the current voxel's predecessor voxel as well as all neighbor voxels that are also neighbor voxels of the current voxel's predecessor voxel. In this process, the number of voxels eligible to be in the group of voxels considered to the current voxel's successor voxel differs according to whether current voxel is adjacent to, on a 2D diagonal to or on a 3D diagonal to its predecessor voxel.

Where the current voxel's predecessor voxel, such as the solid voxel illustrated in FIG. 6A, is adjacent to the current voxel, such as the solid voxel illustrated in FIG. 6B, the voxels indicated by light shading are all automatically eliminated from the selection process for the successor voxel to the current voxel. Only the nine non-shaded voxels which are not neighbor voxels of the predecessor voxel define the group of potential successor voxels of the current voxel. In the illustrated adjacent case of FIGS. 6A and 6B, using the notation of FIG. 1B with the current voxel represented as Vx,y,x, the nine voxels that define the group of potential successor voxels of the current voxel are "adjacent neighbor" voxel Vx,y,z+1, "2D diagonal neighbor" voxels Vx,y+1,z+1, Vx,y−1,z+1, Vx+1,y,z+1, Vx−1,y,z+1, and "3D diagonal neighbor" voxels Vx+1,y+1,z+1, Vx−1,y+1,z+1, Vx+1,y−1,z+1, Vx−1,y−1,z+1.

Where the current voxel's predecessor voxel, such as the solid voxel illustrated in FIG. 7A is on a 3D diagonal to the current voxel, such as the solid voxel illustrated in FIG. 7B, the voxels indicated by light shading are all automatically eliminated from the selection process for the successor voxel to the current voxel. Only the nineteen non-shaded voxels which are not neighbor voxels of the predecessor voxel define the group of potential successor voxels of the current voxel. In the illustrated 3D diagonal case of FIGS. 7A and 7B, using the notation of FIG. 1B with the current voxel represented as Vx,y,x, the nineteen voxels that define the group of potential successor voxels of the current voxel are "adjacent neighbor" voxels Vx−1,y,z, Vx,y+1,z, and Vx,y,z+1; "2D diagonal neighbor" voxels Vx+1,y+1,z, Vx−1,y+1,z, Vx−1,y−1,z, Vx,y+1,z+1, Vx,y−1,z+1, Vx+1,y,z+1, Vx−1,y,z+1, Vx,y+1,z−1, and Vx−1,y,z−1; and "3D diagonal neighbor" voxels Vx+1,y+1,z+1, Vx−1,y+1,z+1, Vx+1,y−1,z+1, Vx−1,y−1,z+1, Vx+1,y+1,z−1, Vx−1,y+1,z−1, and Vx−1,y−1,z−1.

Where the current voxel's predecessor voxel, such as the solid voxel illustrated in FIG. 8A is on a 2D diagonal to the current voxel, such as the solid voxel illustrated in FIG. 8B, the voxels indicated by light shading are all automatically eliminated from the selection process for the successor voxel to the current voxel. Only the fifteen non-shaded voxels which are not neighbor voxels of the predecessor voxel define the group of potential successor voxels of the current voxel. In the illustrated 2D diagonal case of FIGS. 8A and 8B, using the notation of FIG. 1B with the current voxel represented as Vx,y,x, the fifteen voxels that define the group of potential successor voxels of the current voxel are "adjacent neighbor" voxels Vx,y+1,z and Vx,y,z+1; "2D diagonal neighbor" voxels Vx+1,y+1,z, Vx−1,y+1,z, Vx,y+1,z+1, Vx,y−1,z+1, Vx+1,y,z+1, Vx−1,y,z+1, and Vx,y+1,z−1; and "3D diagonal neighbor" voxels Vx+1,y+1,z+1, Vx−1,y+1,z+1, Vx+1,y−1,z+1, Vx−1,y−1,z+1, Vx+1,y+1,z−1, and Vx−1,y+1,z−1.

For any given voxel, to reach an adjacent neighbor voxel, there are six options. For any given voxel, to reach a 3D diagonal neighbor voxel, there are eight options. For any given voxel, to reach a 2D diagonal neighbor voxel, there are twelve options. Accordingly, according to the example inventive method of selecting successor voxels, the average number of voxels considered in successor selection is 14.8, i.e. (6*9+8*19+12*15)/26=14.8) in comparison to the 26 voxels considered in the conventional method.

Figure 5:
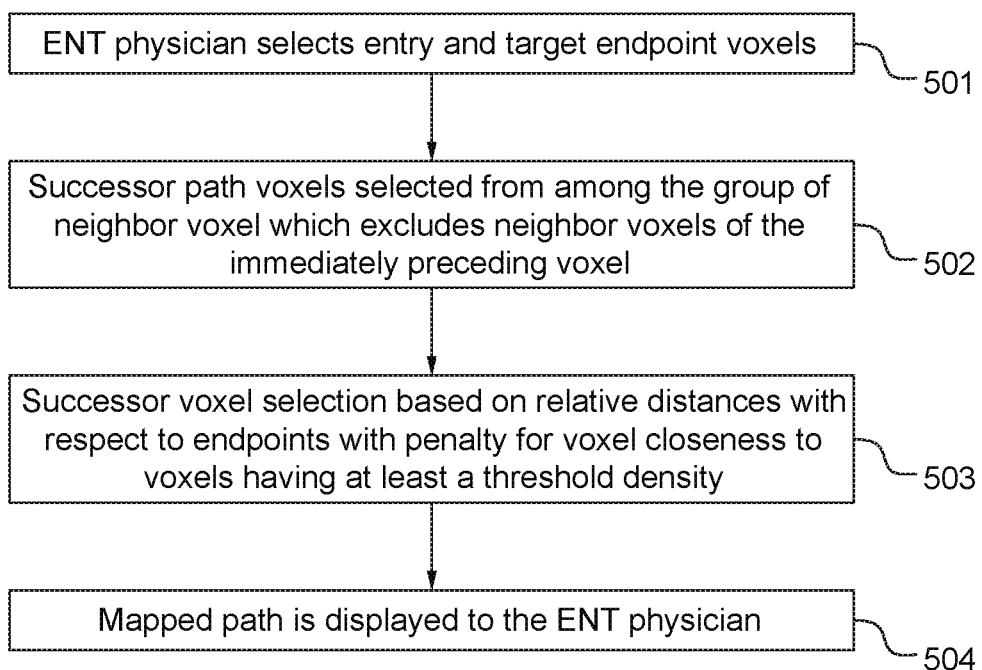
FIG. 5 is a flowchart for deriving the surgical path between endpoints illustrated in FIG. 4 in accordance with teachings of the present invention.

Generally the process proceeds in accordance with the steps of FIG. 5. In a first step 501, the ENT physician selects entry and target endpoint voxels. In a second step 502, for each path voxel having an immediately preceding path voxel, a successor path voxel is selected from among the group of neighbor voxel which excludes neighbor voxels of the immediately preceding voxel. In step 503, Successor voxel selection is made based on relative closeness to the starting endpoint and relative distance from the finishing endpoint with penalty for voxel closeness to voxels having at least a threshold density. In step 504, the mapped path is displayed to the ENT physician.

More specifically, a method for mapping and displaying a three dimensional (3D) surgical pathway within displayed imaging of cranial structures derived from voxels of a cranial scan of a subject is provided. An initial entry voxel $Vx_e,y_e,z_e$ and a surgical site target voxel $Vx_t,y_t,z_t$ are selected as endpoints of the pathway. A series of voxels are then mapped such that each voxel between the entry voxel $Vx_e,y_e,z_e$ and the target voxel $Vx_t,y_t,z_t$ is a neighbor voxel of both an immediately preceding voxel and an immediately succeeding voxel of the series to define the 3D surgical pathway. For each voxel $Vx_i,y_i,z_i$ in the series having an immediately preceding voxel, the immediately succeeding voxel of voxel $Vx_i,y_i,z_i$ is selected from among the group of neighbor voxel of voxel $Vx_i,y_i,z_i$ which excludes neighbor voxels of the immediately preceding voxel of voxel $Vx_i,y_i,z_i$. The selection includes determining selection weights of each voxel of the group of neighbor voxel on a selected basis including relative distances from the endpoint voxels $Vx_e,y_e,z_e$ and $Vx_t,y_t,z_t$ and relative distance from voxels within a predetermined distance that represent at least a threshold density. The selection is then made by selecting the immediately succeeding voxel of voxel $Vx_i,y_i,z_i$ based on a comparison of the determined selection weights. The voxels of the 3D surgical pathway are then highlighted in a displayed view of the cranial structure to provide a visualization of the 3D surgical pathway.

A further implementation of the invention includes the selection of semi-targets based on an ENT physician's knowledge of cranial structure. For example, a "semi-target" voxels can be selected according to the ENT physician's knowledge of where the path must go as in the case of needing to traverse a narrow passage or the like while the selection may also take into account known cavities. FIG. 9 illustrates a displayed view of a voxel path determined using a semi-target voxel $Vx_{st},y_{st},z_{st}$, in addition to the same entry site voxel $Vx_e,y_e,z_e$ to the same surgical site target voxel $Vx_t,y_t,z_t$, of FIG. 3. The voxels in the determined path of FIG. 9 have been highlighted by processing unit 22 so that a continuous line representing the determined path between the entry site voxel $Vx_e,y_e,z_e$ through the semi-target voxel $Vx_{st},y_{st},z_{st}$, to the target voxel $Vx_t,y_t,z_t$, is displayed.

In the example implementation of the invention that produced the path illustrated in FIG. 9, the process was completed six times faster than simply calculating the path directly between the entry site voxel $Vx_e,y_e,z_e$ and to the target voxel $Vx_t,y_t,z_t$ using the conventional method.

In particular, the method is more highly efficient where voxels representing bone are within a shortest line (Euclidean distance) between the initial entry voxel $Vx_e,y_e,z_e$ and the surgical site target voxel $Vx_t,y_t,z_t$. In such case, a semi-target voxel $Vx_{st},y_{st},z_{st}$ may be advantageously selected between the initial entry voxel $Vx_e,y_e,z_e$ and the surgical site target voxel $Vx_t,y_t,z_t$ such that voxels representing bone are not within a shortest line between the initial entry voxel $Vx_e,y_e,z_e$ and the semi-target voxel $Vx_{st},y_{st},z_{st}$.

As shown in FIG. 9, the example determined path traverses nasal cavities a substantial distance from the illustrated bones where possible. As such, inserting the catheter 38 along the determined path decreases the difficulty of operation of surgical tools at the target site.

Figure 10:
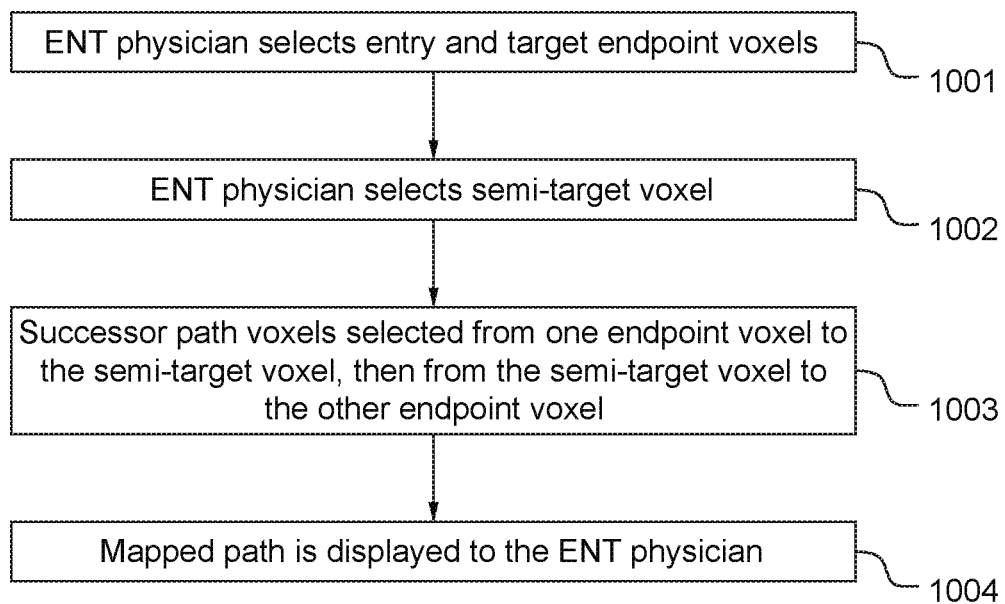
FIG. 10 is a flowchart for deriving the surgical path between endpoints illustrated in FIG. 9 in accordance with teachings of the present invention.

Generally the process proceeds in accordance with the steps of FIG. 10. In a first step 1001, the ENT physician selects entry and target endpoint voxels. In a second step 1002, the ENT physician selects a semi-target voxel between the endpoint voxels. In step 1003, successor voxel selection is made from one endpoint voxel to the semi-target voxel, then from the semi-target voxel to the other endpoint voxel. In step 1004, the mapped path is displayed to the ENT physician.

More specifically, a further method for mapping and displaying a three dimensional (3D) surgical pathway within displayed imaging of cranial structures derived from voxels of a cranial scan of a subject is provided. An initial entry voxel $Vx_e,y_e,z_e$ and a surgical site target voxel $Vx_t,y_t,z_t$ are selected where voxels representing bone are within the shortest path between the initial entry voxel $Vx_e,y_e,z_e$ and the surgical site target voxel $Vx_t,y_t,z_t$. A semi-target voxel $Vx_{st},y_{st},z_{st}$ is also selected between the initial entry voxel $Vx_e,y_e,z_e$ and the surgical site target voxel $Vx_t,y_t,z_t$. A series of voxels is mapped that includes the semi-target voxel $Vx_{st},y_{st},z_{st}$ such that each voxel between the entry voxel $Vx_e,y_e,z_e$ and the target voxel $Vx_t,y_t,z_t$ is a neighbor voxel of both an immediately preceding voxel and an immediately succeeding voxel of the series to define the 3D surgical pathway.

For each voxel $Vx_i,y_i,z_i$ in the series between the initial entry voxel $Vx_e,y_e,z_e$ and the semi-target voxel $Vx_{st},y_{st},z_{st}$, the immediately succeeding voxel of voxel $Vx_i,y_i,z_i$ is selected from among the group of neighbor voxels of voxel $Vx_i,y_i,z_i$. The selection includes determining selection weights of each voxel of the group of neighbor voxels on a selected basis including relative distances from the entry voxel $Vx_e,y_e,z_e$ and the semi-target voxel $Vx_{sc},y_{st},z_{st}$. The immediately succeeding voxel of voxel $Vx_i,y_i,z_i$ is selected based on a comparison of the determined selection weights.

For each voxel $Vx_i,y_i,z$ in the series between the semi-target voxel $Vx_{st},y_{st},z_{st}$ and the target voxel $Vx_t,y_t,z_t$, the immediately succeeding voxel of voxel $Vx_j,y_j,z_j$ is selected from among the group of neighbor voxel of voxel $Vx_j,y_j,z_j$. The selection includes determining selection weights of each voxel of the group of neighbor voxel on a selected basis including relative distances from the semi-target voxel $Vx_{st},y_{st},z_{st}$ and the target voxel $Vx_t,y_t,z_t$. The immediately succeeding voxel of voxel $Vx_j,y_j,z_j$ is selected based on a comparison of the determined selection weights.

The selected path voxels are selectively highlighted and the voxels of the 3D surgical pathway in a displayed view of the cranial structure to provide a visualization of the 3D surgical pathway.

The implementation employing semi-targets can be combined with the use of the example modified A-Star algorithm disclosed above. In such case, for each voxel $Vx_i,y_i,z_i$ in the series, the immediately succeeding voxel of voxel $Vx_i,y_i,z_i$ is selected from among the group of neighbor voxels of voxel $Vx_i,y_i,z_i$ which excludes neighbor voxels of the immediately preceding voxel of voxel $Vx_i,y_i,z_i$. The determining of selection weights of neighbor voxels of each voxel $Vx_i,y_i,z_i$ includes penalties based on relative distance from voxels within a predetermined distance that represent at least a threshold density. For each voxel $Vx_j,y_j,z_j$ in the series, the immediately succeeding voxel of voxel $Vx_j,y_j,z_j$ is selected from among the group of neighbor voxels of voxel $Vx_j,y_j,z_j$ which excludes neighbor voxels of the immediately preceding voxel of voxel $Vx_j,y_j,z_j$. The determining of selection weights of neighbor voxels of each voxel $Vx_j,y_j,z_j$ includes penalties based on relative distance from voxels within the predetermined distance that represent at least the threshold density.

Any of the functions and methods described herein can be implemented in a general-purpose computer, a processor, or a processor core. Suitable processors include, by way of example, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), and/or a state machine. Such processors can be manufactured by configuring a manufacturing process using the results of processed hardware description language (HDL) instructions and other intermediary data including netlists (such instructions capable of being stored on a computer-readable media). The results of such processing can be maskworks that are then used in a semiconductor manufacturing process to manufacture a processor which implements features of the disclosure.

Any of the functions and methods described herein can be implemented in a computer program, software, or firmware incorporated in a non-transitory computer-readable storage medium for execution by a general-purpose computer or a processor. Examples of non-transitory computer-readable storage mediums include a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs).

It should be understood that many variations are possible based on the disclosure herein. Although features and elements are described above in particular combinations, each feature or element can be used alone without the other features and elements or in various combinations with or without other features and elements.

The invention claimed is:

1. A method for mapping and displaying a three dimensional (3D) surgical pathway within displayed imaging of cranial structures derived from voxels of a cranial scan of a subject, the method comprising:
    selecting an initial entry voxel $Vx_e,y_e,z_e$ and a surgical site target voxel $Vx_t,y_t,z_t$ as endpoints of the 3D surgical pathway;
    mapping a series of voxels such that each voxel between the entry voxel $Vx_e,y_e,z_e$ and the target voxel $Vx_t,y_t,z_t$ is a neighbor voxel of both an immediately preceding voxel and an immediately succeeding voxel of the series to define the 3D surgical pathway;
    for each voxel $Vx_i,y_1,z_i$ in the series having an immediately preceding voxel, selecting the immediately succeeding voxel of voxel $Vx_i,y_i,z_i$ from among a group of neighbor voxels of voxel $Vx_i,y_1,z_i$ which excludes neighbor voxels of the immediately preceding voxel of voxel $Vx_i,y_1,z_i$ including:
        determining selection weights of each voxel of the group of neighbor voxels on a selected basis including relative distances with respect to the endpoint voxels $Vx_e,y_e,z_e$ and $Vx_t,y_t,z_t$ and relative distance from voxels within a predetermined distance that represent at least a threshold density; and selecting the immediately succeeding voxel of voxel $Vx_i, y_i, z_i$ based on a comparison of the determined selection weights; and selectively highlighting the voxels of the 3D surgical pathway in a displayed view of the cranial structure to provide a visualization of the 3D surgical pathway.

2. The method of claim 1 wherein:

the selected basis for the determining selection weights for a voxel includes a penalty where a voxel that represents at least the threshold density is within the predetermined distance.

3. The method of claim 2 wherein the penalty is based on the difference between the predetermined distance and the distance of the voxel from a closest voxel that represents at least the threshold density;

the threshold density is set as minus five hundred (−500) Hu; and the predetermined distance is 0.8 mm.

4. The method of claim 1 wherein:

the 3D surgical pathway is determined starting at the entry voxel $Vx_e, y_e, z_e$;

the determining selection weights of each voxel of the group of neighbor voxels of each voxel $Vx_i, y_i, z_i$ on a selected basis includes relative closeness to the entry voxel $Vx_e, y_e, z_e$ and relative distance from the target voxel $Vx_t, y_t, z_t$; and the selected basis for the determining selection weights for a voxel includes a penalty based on the difference between the predetermined distance and the distance of the voxel from the closest voxel that represents at least the threshold density.

5. The method of claim 4 wherein:

the penalty is based on the difference between the predetermined distance and the distance of the voxel from the closest voxel that represents at least the threshold density;

the threshold density is set as minus five hundred (−500) Hu; and the predetermined distance is 0.8 mm.

6. The method of claim 1 wherein:

the 3D surgical pathway is determined starting at the target voxel $Vx_t, y_t, z_t$; and the determining selection weights of each voxel of the group of neighbor voxels of each voxel $Vx_i, y_1, z_i$ on a selected basis includes relative distance from the entry voxel $Vx_e, y_e, z_e$ and relative closeness to the target voxel $Vx_t, y_t, z_t$; and the selected basis for the determining selection weights for a voxel includes a penalty based on the difference between the predetermined distance and the distance of the voxel from a closest voxel that represents at least the threshold density.

7. The method of claim 6 wherein:

the penalty is based on the difference between the predetermined distance and the distance of the voxel from the closest voxel that represents at least the threshold density;

the threshold density is set as minus five hundred (−500) Hu; and the predetermined distance is 0.8 mm.

8. The method of claim 1 wherein the threshold density is set to be the density of bone.

9. The method of claim 1 wherein the selectively highlighting of the voxels of the 3D surgical pathway in a displayed view of the cranial structure includes applying different highlighting of voxels of portions of the 3D surgical pathway that are hidden in the displayed view.

10. The method of claim 1 further comprising:

using the displayed view of the 3D surgical pathway to insert a distal end of a catheter into the cranium of the subject along the 3D surgical pathway, starting at a physical location in the subject's cranium corresponding to the initial entry voxel $Vx_e, y_e, z_e$, to deploy the distal end of the catheter to a physical location corresponding to the surgical site target voxel $Vx_t, y_t, z_t$.

11. An apparatus for mapping and displaying a three dimensional (3D) surgical pathway within a graphic display of a cranial structure derived from voxels of a cranial scan of a subject, the apparatus comprising:

data storage configured to store voxels of the cranial scan of the subject;

a processor and an associated display device configured to provide sectional and perspective views of cranial structures of the subject based on the cranial scan;

a voxel selection device configured for a user to select an initial entry voxel $Vx_e, y_e, z_e$ and a surgical site target voxel $Vx_t, y_t, z_t$ as endpoints of the 3D surgical pathway;

the processor configured to map a series of voxels such that each voxel between the entry voxel $Vx_e, y_e, z_e$ and the target voxel $Vx_t, y_t, z_t$ is a neighbor voxel of both an immediately preceding voxel and an immediately succeeding voxel of the series to define the 3D surgical pathway;

for each voxel $Vx_i, y_1, z_i$ in the series having an immediately preceding voxel, the processor configured to select the immediately succeeding voxel of voxel $Vx_i, y_i, z_i$ from among a group of neighbor voxels of voxel $Vx_i, y_1, z_i$ which excludes neighbor voxels of the immediately preceding voxel of voxel $Vx_i, y_i, z_i$, by:

determining selection weights of each voxel of the group of neighbor voxels on a selected basis including relative distances with respect to the endpoint voxels $Vx_e, y_e, z_e$ and $Vx_t, y_t, z_t$ and relative distance from voxels within a predetermined distance that represent at least a threshold density; and selecting the immediately succeeding voxel of voxel $Vx_i, y_i, z_i$ based on a comparison of the determined selection weights; and the processor configured to selectively highlight the voxels of the 3D surgical pathway in imaging of cranial structures on the display device to provide a visualization of the 3D surgical pathway.

12. The apparatus of claim 11 wherein the processor is configured such that the selected basis used by the processor for the determining selection weights for a voxel includes a penalty where a voxel that represents at least the threshold density is within the predetermined distance.

13. The apparatus of claim 12 wherein the processor is configured such that:

the penalty is based on the difference between the predetermined distance and the distance of the voxel from a closest voxel that represents at least the threshold density;

the threshold density is set as minus five hundred (−500) Hu; and the predetermined distance is 0.8 mm.

14. The apparatus of claim 11 wherein the processor is configured such that:

the 3D surgical pathway is determined starting at the entry voxel $Vx_e, y_e, z_e$;

selection weights of each voxel of the group of neighbor voxels of each voxel $Vx_i, y_1, z_i$ are determined on a selected basis includes relative closeness to the entry voxel $Vx_e, y_e, z_e$ and relative distance from the target voxel $Vx_t, y_t, z_t$; and the selected basis used by the processor for the determining selection weights for a voxel includes a penalty based on the difference between the predetermined distance and the distance of the voxel from the closest voxel that represents at least the threshold density.

15. The apparatus of claim 14 wherein the processor is configured such that:

the penalty is based on the difference between the predetermined distance and the distance of the voxel from the closest voxel that represents at least the threshold density;

the threshold density is set as minus five hundred (−500) Hu; and the predetermined distance is 0.8 mm.

16. The apparatus of claim 11 wherein the processor is configured such that:

the 3D surgical pathway is determined starting at the target voxel $Vx_t, y_t, z_t$; and selection weights of each voxel of the group of neighbor voxels of each voxel $Vx_i, y_i, z_i$ are determined on a selected basis includes relative distance from the entry voxel $Vx_e, y_e, z_e$ and relative closeness to the target voxel $Vx_t, y_t, z_t$; and the selected basis used by the processor for the determining selection weights for a voxel includes a penalty based on the difference between the predetermined distance and the distance of the voxel from a closest voxel that represents at least the threshold density.

17. The apparatus of claim 16 wherein the processor is configured such that:

the penalty is based on the difference between the predetermined distance and the distance of the voxel from the closest voxel that represents at least the threshold density;

the threshold density is set as minus five hundred (−500) Hu; and the predetermined distance is 0.8 mm.

18. The apparatus of claim 11 wherein the processor is configured such that the threshold density is set to be the density of bone.

19. The apparatus of claim 11 wherein the processor is configured such that the selectively highlighting of the voxels of the 3D surgical pathway in a displayed view of the cranial structure includes applying different highlighting of voxels of portions of the 3D surgical pathway that are hidden in the displayed view.

20. The apparatus of claim 1 further comprising a catheter having a distal end from which a surgical tool can be operated;

associated catheter location sensing equipment coupled to the processor;

the location sensing equipment configured to provide signals that enable the processor to track the location of the distal end of the catheter as it is inserted into the subject's cranium; and the processor configured to control the display device to display a corresponding visualization of catheter travel such that a user is enabled to use a displayed view of the 3D surgical pathway to insert the distal end of the catheter into the cranium of the subject along the 3D surgical pathway, starting at a physical location in the subject's cranium corresponding to the initial entry voxel $Vx_e, y_e, z_e$, to deploy the distal end of the catheter to a physical location corresponding to the surgical site target voxel $Vx_t, y_t, z_t$.

* * * * *

UNITED STATES PATENT AND TRADEMARK OFFICE
CERTIFICATE OF CORRECTION

PATENT NO. : 11,771,505 B2
APPLICATION NO. : 16/731524
DATED : October 3, 2023
INVENTOR(S) : Yair Palti et al.

Page 1 of 2

It is certified that error appears in the above-identified patent and that said Letters Patent is hereby corrected as shown below:

On the Title Page
In Item (72), under "Inventors", in Column 1, Line 1, delete "Herzelia" and insert -- Herzliya --, therefor.

In the Specification
In Column 1, Line 44, delete "patients" and insert -- patient's --, therefor.
In Column 3, Line 31, delete "0.8 mm.14." and insert -- 0.8 mm. --, therefor.
In Column 4, Line 54, delete "with in" and insert -- within --, therefor.
In Column 5, Line 40, delete "displayed the" and insert -- displayed in the --, therefor.
In Column 6, Line 10, delete "On" and insert -- One --, therefor.
In Column 6, Line 20, delete "an to" and insert -- and to --, therefor.
In Column 6, Line 29, delete "39 the" and insert -- 39 and the --, therefor.
In Column 7, Line 10, delete "such a" and insert -- such as --, therefor.
In Column 7, Line 14, delete "voxel the" and insert -- voxel and the --, therefor.
In Column 7, Line 17, delete "in the" and insert -- the --, therefor.
In Column 7, Line 24, delete "the the" and insert -- the --, therefor.
In Column 10, Line 1, delete "14.8)" and insert -- 14.8 --, therefor.
In Column 11, Line 40, delete "Vxscyst,zst." and insert -- Vxst,yst,zst. --, therefor.
In Column 11, Line 43, delete "Vxi,yi,z" and insert -- Vxj,yj,zj --, therefor.
In Column 11, Line 54, delete "in a" and insert -- are in a --, therefor.

In the Claims
In Column 12, Line 58, in Claim 1, delete "Vxi,y1,zi" and insert -- Vxi,yi,zi --, therefor.
In Column 12, Line 61, in Claim 1, delete "Vxi,y1,zi" and insert -- Vxi,yi,zi --, therefor.
In Column 12, Line 63, in Claim 1, delete "Vxi,y1,zi" and insert -- Vxi,yi,zi --, therefor.
In Column 13, Line 47, in Claim 6, delete "Vxi,y1,zi" and insert -- Vxi,yi,zi --, therefor.
In Column 14, Line 31, in Claim 11, delete "Vxi,y1,zi" and insert -- Vxi,yi,zi --, therefor.
In Column 14, Line 35, in Claim 11, delete "Vxi,y1,zi" and insert -- Vxi,yi,zi --, therefor.
In Column 14, Line 67, in Claim 14, delete "Vxe,ye,ze," and insert -- Vxe,ye,ze; --, therefor.

Signed and Sealed this
Thirteenth Day of February, 2024

*Katherine Kelly Vidal*

Katherine Kelly Vidal
*Director of the United States Patent and Trademark Office*

In Column 15, Line 2, in Claim 14, delete "Vxi,y1,zi" and insert -- Vxi,yi,zi --, therefor.
In Column 16, Line 16, in Claim 20, delete "comprising" and insert -- comprising: --, therefor.